United States Patent [19]
Dunn et al.

[11] 3,968,226
[45] July 6, 1976

[54] 3-HETEROCYCLIC THIOMETHYLCEPHALOSPORINS AS ANTIBACTERIAL AGENTS

[75] Inventors: George L. Dunn, Wayne; John R. E. Hoover, Glenside, both of Pa.

[73] Assignee: SmithKline Corporation, Philadelphia, Pa.

[22] Filed: Sept. 30, 1974

[21] Appl. No.: 510,191

Related U.S. Application Data

[60] Division of Ser. No. 262,903, June 14, 1972, which is a continuation-in-part of Ser. No. 116,598, Feb. 18, 1971, which is a continuation-in-part of Ser. No. 99,296, Dec. 17, 1970, abandoned.

[52] U.S. Cl. .............................................. 424/246
[51] Int. Cl.² ......................................... A61K 31/54
[58] Field of Search .................................... 424/246

[56] References Cited
UNITED STATES PATENTS

| | | | |
|---|---|---|---|
| 3,489,752 | 1/1970 | Crase | 260/243 C |
| 3,516,997 | 6/1970 | Takano et al. | 260/243 C |
| 3,641,021 | 2/1972 | Ryan | 260/243 C |
| 3,644,347 | 2/1972 | Webber et al. | 260/243 C |

*Primary Examiner*—Jerome D. Goldberg
*Attorney, Agent, or Firm*—Stuart R. Suter; William H. Edgerton; Alan D. Lourie

[57] ABSTRACT

Cephalosporin compounds substituted at the 7-position with free or substituted α-aminophenylacetamido and at the 3-position with a heterocyclic thiomethyl group are prepared by displacement of a 3-acetoxymethyl compound with a mercaptoheterocycle. The products are antibacterial agents.

10 Claims, No Drawings

3-HETEROCYCLIC THIOMETHYLCEPHALOSPORINS AS ANTIBACTERIAL AGENTS

This is a division of application Ser. No. 116,598, filed Feb. 18, 1971, which application was a continuation-in-part of application Ser. No. 99,296, filed Dec. 17, 1970, now abandoned.

This invention relates to chemical compounds known as cephalosporins, which compounds possess antibacterial activity.

The compounds of this invention are represented by the following structural formula:

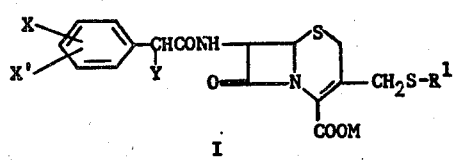

I in which:
X and X' are each hydrogen, lower alkyl of 1–4 carbon atoms, lower alkoxy of 1–4 carbon atoms, hydroxy, hydroxmethyl, halo, nitro, amino, aminomethyl or trifluoromethyl;
Y is $NH_2$ or NHR;
R is hydrogen, aminoalkanoyl of up to 6 carbon atoms, where the alkanoyl group may be branched or straight chain and may be unsubstituted or substituted with hydroxy, mercapto, methylthio, carboxy, amino or phenyl; substituted or unsubstituted alkanoyl of up to 8 carbon atoms, where the substituent may be lower alkoxy of up to 4 carbon atoms, hydroxy, allyloxy, lower alkylthio of up to 4 carbon atoms, azido, halo, cyano, carboxy, carbalkoxy where said alkoxy has up to 4 carbon atoms, or phenoxy; carbocyclic acyl which may be unsubstituted or substituted with lower alkyl or alkoxy of up to 4 carbon atoms, halo, nitro, trifluoromethyl, hydroxy, amino, cyano, or dilower alkylamino of 2–8 carbon atoms; or heterocyclic acyl which may be unsubstituted or substituted with methyl;
$R^1$ is a 5 or 6 membered heterocyclic ring containing one or more atoms of N, O or S, with or without ring substituents such as lower alkyl, cycloalkyl or alkenyl of up to 6 carbons, lower alkoxy of up to 4 carbons, lower alkoxyalkyl, $CF_3$, $NH_2$, alkylamino, dialkylamino, phenyl, methylthio, or halogen, such as

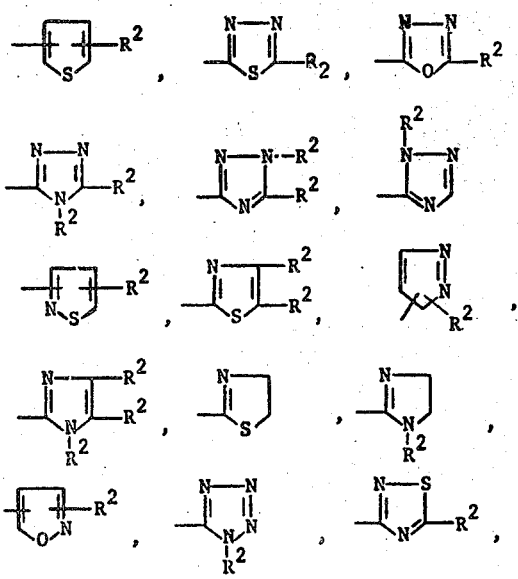

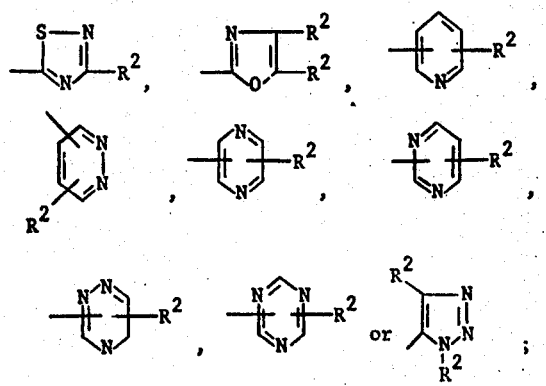

$R_2$ is hydrogen; halogen; lower alkyl, cycloalkyl or alkenyl, each of up to 6 carbon atoms; $CF_3$; $NH_2$; $NHR^3$; $NR^3_2$; phenyl; lower alkoxy, alkoxyalkyl, each alkyl or alkoxy of up to 4 carbon atoms; or $SCH_3$; in any combination;
$R^3$ is hydrogen or lower alkyl of up to 4 carbon atoms; and
M is hydrogen or an alkali metal.

A preferred group of compounds within the scope of Formula I is that in which X is p—HO, X' is H and Y is $NH_2$. These compounds have highly advantageous properties as antibacterial agents.

The compounds of the present invention are prepared by reaction of a compound differing from one of Formula I in that the 3-substituent is acetoxymethyl rather than $R^1$-thiomethyl, with a mercaptoheterocycle. The reaction is preferably conducted at a pH near neutrality. The solvent is preferably water. The reaction may be carried out at temperatures from about room temperature to the boiling point of the solvent, the time of reaction varying with the particular temperature, solvent and reactants. The reaction product is isolated by careful acidification of the reaction mixture and extraction with an appropriate organic solvent. The amino starting material should be protected with a readily removable group subh as t-butoxycarbonyl, carbobenzyloxy or trichloroethoxycarbonyl. The displacement at the 3-position is then conducted, followed by removal of the protective group in the conventional manner.

Compounds of Formula I where Y is NHR also are prepared by displacement of a compound with a 3-acetoxymethyl group. The amino group first is protected with an easily removable group such as t-butoxycarbonyl, carbobenzyloxy, or trichloroethoxycarbonyl, and, after the displacement at the 3-position, the protective group removed by known methods. Substitution of the amino group to give compounds where Y is NHR is then carried out by known methods.

It is recognized that due to the asymmetric α-carbon in the 7-acetamido group optical isomers will exist. The D isomer is the preferred isomer; however, the L isomer and the racemic mixture are also within the scope of this invention.

The starting materials for preparing the products of this invention are known, readily preparable by known methods, or described herein.

The products of this invention are antibacterial agents active against Gram-negative and Gram-positive organisms such as Staph. aureus, Strep. pyogenes, Strep. faecalis, Diplococcus pneumoniae, E. coli, Klebsiella pneumoniae, Salmonella, Serratia sp., Shigella, and Enterobacter aerogenes. A large number of compounds within the scope of Formula I have been prepared and all have had antibacterial activity in an in vitro testing program. Compounds were X is p-OH and X' is H are especially advantageous in that they exhibit higher blood levels and lower $PD_{50}$'s than related compounds.

The compounds are formulated into injectable or oral formulations in the same manner as other cephalosporin antibiotics. They are administered by injection or orally to prevent and treat bacterial infections in doses which will vary with the nature and severity of the infection and the age, weight, and condition of the subject.

The following examples are intended to illustrate the preparation of the products of the invention, but are not to be construed as limiting the scope thereof. Temperatures are in degrees Centigrade.

EXAMPLE 1

7-(D-α-Aminophenylacetamido)-3-(5-methyl-1,3,4-thiadiazol-2-ylthiomethyl)-3-cephem-4-carboxylic acid A solution of 7-(D-α-t-butoxycarboxamidophenylacetamido)cephalosporanic acid (1.82 g., 3.59 mmol.) [J. L. Spenser et al., J. Med. Chem. 9:746 (1966)] and 2-mercapto 5-methyl-1,3,4-thiadiazole (0.50 g., 3.78 mmole) [J. Sandström and I. Wennerbeck, *Acta. Chem. Scand.* 20:57 (1966)]in 33 ml. of phosphate buffer (pH 6.2) containing bicarbonate (0.315 g., 3.78 mmol.) was heated at 57° for 23 hours. The cloudy solution was cooled to room temperature and extracted with ethyl acetate. The aqueous phase was cooled in ice, layered with ethyl acetate and acidified to pH 2.0 with 3N hydrochloric acid. The aqueous phase was extracted again with ethyl acetate and the combined, dried ($MgSO_4$) organic layers were evaporated in vacuo to give 0.79 g. (38%) of desired product as the free acid of the t-butoxycarboxamidophenylacetamidocephalosporin. A portion of the crude product (0.5 g.) was reprecipitated by dissolving it in 5% aqueous sodium bicarbonate solution followed by acidification to give the free acid (0.22 g.) as an off-white solid: m.p. 160° (dec.).

The sodium salt was prepared by treating a solution of the acid in isopropyl alcohol with a solution containing a slight excess of sodium 2-ethylhexanoate in isopropyl alcohol.

The t-butoxycarbonyl derivative (0.22 g.), prepared as described above, was dissolved in 3 ml. of cold trifluoroacetic acid and the solution was stirred for 30 minutes at room temperature. The excess trifluoroacetic acid was evaporated in vacuo at room temperature and the glassy residue obtained was triturated with ether to give 77 mg. of the trifluoroacetate salt of the title compound: IR (nujol) 5.65 μ (β-lactam).

The trifluoroacetate salt (77 mg.) was converted to the zwitterionic form by dissolving the salt in 3 ml. of water and stirring the solution at room temperature with 3 ml. of a 25% solution of Amberlite LA-1 (acetate form) in methyl isobutyl ketone for 2 hours. The layers were separated and the aqueous phase was evaporated at 30° in vacuo to give 47 mg. of desired product; m.p. 160° (dec.); IR (nujol) 5.65 μ (β-lactam).

Calculated for $C_{19}H_{19}N_5O_4S_3 \cdot H_2O$: C, 46.05; H, 4.27; N, 14.13; Found: C, 46.12; H, 4.51; N, 14.14.

EXAMPLE 2

3-(3,4-Dimethyl-1,2,4-triazol-5-ylthiomethyl)-7-(D-2-aminophenylacetamido)-3-cephem-4-carboxylic acid To a solution of $NaHCO_3$ (4.2 g., 0.05 mol.) in water (50 ml.) was added 7-ACA (6.8 g., 0.025 mol.), water (50 ml.) and acetone (25 ml.). The resulting solution was warmed to 45° and then a solution of 3,4-dimethyl-5-mercapto-1,2,4-triazole (5.0 g., 0.038 mol.) in acetone (50 ml.) and 5% $NaHCO_3$ (10 ml.) was added. The reaction was refluxed until the reaction was completed as determined by the disappearance of the acetoxy carbonyl band in the infrared absorption spectrum. During this time the pH was maintained at ca. 7.6. The solution was cooled to 10° and adjusted to pH 3.5 with 3N HCl. The precipitated product was collected, washed with acetone, and dried to give a 60% yield of 3-(3,4-dimethyl-1,2,4-triazol-5-ylthiomethyl)-7-amino-3-cephem-4-carboxylic acid.

To a cold solution (−10°) of D-α-t-butoxycarboxamidophenylacetic acid (2.26 g., 0.013 mol.) and triethylamine (1.4 ml., 0.013 mol.) in dry tetrahydrofuran (50 ml.) was added with stirring isobutyl chloroformate (1.5 ml., 0.013 mol.) over a 10 minute period. To this was added dropwise at −10° a cold solution of the above 7-ACA derivative triethylamine salt [prepared by adding triethylamine (1.5 ml., 0.013 mole) to a suspension of 7-ACA compound (5.0 g., 0.013 mol.) in 40 ml. 50% aq. tetrahydrofuran]. The reaction solution was stirred 1 hour at 0° and 1.5 hours at room temperature. The tetrahydrofuran was evaporated, water added to the mixture, and extracted with ethyl acetate. The organic layer was discarded. The aqueous phase was cooled, layered with ethyl acetate, and acidified to pH 3 using 3N HCl. The phases were separated and the aqueous phase was extracted with ethyl acetate. Evaporation of the combined and dried organic layers gave a solid. Trituration with ether-petroleum ether followed by recrystallization from methylene chloride-ether gave the pure t-butoxycarbonyl derivative.

The above product (6.5 g.) was added to cold trifluoroacetic acid (65 ml.) and stirred at 0°. The solution was poured slowly into a large volume of ether and the precipitated trifluoroacetate salt was collected. Alternatively, the trifluoroacetate salt may be isolated by evaporating the excess trifluoroacetic acid and triturating the residue with ether.

The trifluoroacetate salt (5.3 g.) was dissolved in water (25 ml.) and 15 g. of a polystyrene-amine ion-exchange resin, Amberlite IR-45, was added. After stirring 1 hour at room temperature the resin was filtered off and the aqueous solution was lyophilized to yield the title compound.

An alternative procedure to obtain the zwitterion involved dissolution of the trifluoroacetate salt in water, addition of methyl isobutyl ketone (MIBK) and, while stirring, adjustment of the solution to pH 4 using tri-n-butylamine. The solid product was collected, washed with MIBK and ethyl acetate, and dried.

Calculated for $C_{20}H_{22}N_6O_4S_2 \cdot 1.5H_2O$: C, 47.89; H, 5.02; N, 16.75; Found: C, 48.03; H, 4.66; N, 16.75.

EXAMPLE 3

7-(D-2-Aminophenylacetamido)-3-(3-methylthio-1,2,4-thiadiazol-5-ylthiomethyl)-3-cephem-4-carboxylic acid 7-Amino-3-(3-methylthio-1,2,4-thiadiazol-5-ylthiomethyl)-3-cephem-4-carboxylic acid was prepared according to the first paragraph of Example 2 using 5-mercapto-3-methylthio-1,2,4-thiadiazole.

To a cooled solution of N-t-butoxycarbonyl-2-phenylglycine (5.02 g., 0.02 mol.) and N-hydroxysuccinimide (2.3 g., 0.02 mol.) in dry tetrahydrofuran was added dicyclohexylcarbodiimide (4.12 g., 0.02 mol.). After stirring 7 hours at ice bath temperature, the reaction was allowed to stand overnight at room temperature. The dicyclohexylurea was removed by filtration and the filtrate evaporated to yield the succinimide ester.

To a cooled solution of the 7-aminocephem compound (6.87 g., 0.017 mol.) in dry pyridine (120 ml.) containing triethylamine (5.1 ml.) was added the succinimide ester (6.32 g., 0.018 mol.). The reaction was stirred 4.5 hours at room temperature and then poured into water (250 ml.). Adjustment of the solution to pH 2 precipitated the t-BOC protected compound which collected, washed with water and dried.

The above O: gave the zwitterionic title compound after it was treated with cold trifluoroacetic acid for 5 minutes and then was isolated as described in Example 2 using the tributylamine procedure; m.p. 150° (dec.);

Calculated for $C_{19}H_{19}N_5O_4S_4.H_2O$: C, 43.25; H, 4.01; N, 13.27; Found: C, 43.28; H, 3.8; N, 13.30.

EXAMPLE 4

7-(2-Aminophenylacetamido)-3-(1-butyltetrazol-5-ylthiomethyl)-3-cephem-4-carboxylic acid 7-Amino-3-(1-butyltetrazol-5-ylthiomethyl)-3-cephem-4-carboxylic acid was prepared in 70% yield according to the procedure of Example 2.

To a stirred suspension of 0.04 moles of this 7-amino compound in 80 ml. of $CH_2Cl_2$, cooled to 5°, there was slowly added 10.9 ml. (0.08 moles) of triethylamine. There was soon added a solution of 16.7 g. (0.04 moles) of D-(-)-N-t-butoyxycarbonylphenylglycine 2,4-dinitrophenyl ester in 20 ml. of $CH_2Cl_2$. After stirring at 25° overnight, the $CH_2Cl_2$ was removed under vacuum ( ≤ 20°), and 500 ml. of ethyl acetate added to the residue. The resulting solution was washed with 100 ml. of 1N HCl, the organic layer separated and dried, and the solvent removed to give 7-N-t-butoxycarbonylaminophenylacetamido-3-(1-butyltetrazol-5-ylthiomethyl)-3-cephem-4-carboxylic acid.

This acid was converted to the free amino product by reaction with cold trifluoroacetic acid (1:10 w/v) for 20 minutes. Excess trifluoroacetic acid was removed in the cold, and the residue triturated with ether to give the trifluoroacetate salt as a white solid. This salt was dissolved in a small amount of water to which a drop of concentrated HCl had been added, and any insoluble material filtered off. The filtrate was basified to pH 3.9 and the product collected by filtration; m.p. 160°-170° (dec.).

EXAMPLE 5

7-(D-2-Aminophenylacetamido)-3-(thien-2-ylthiomethyl)-3-cephem-4-carboxylic acid The title compound was obtained by using 2-mercaptothiophene in the procedure of Example 2; m.p. 163°-167° (dec.);

Calculated for $C_{20}H_{19}N_3O_4S_3.1.5\ H_2O$: C, 49.16; H, 4.54; N, 8.60; Found: C, 48.97; H, 4.19; N, 8.63.

EXAMPLE 6

7-(D-2-Aminophenylacetamido)-3-(4-methyloxazol-2-ylthiomethyl)-3-cephem-4-carboxylic acid The zwitterionic title compound was obtained by using 2-mercapto-4-methyloxazole in the procedure of Example 2 except ammonium hydroxide was substituted in the tributylamine isolation method; m.p. 195°-200° (dec.);

Calculated for $C_{20}H_{20}N_4O_5S_2.\frac{1}{2}\ H_2O$: C, 51.16; H, 4.51; N, 11.93; Found: C, 51.18; H, 4.67; N, 11.55.

EXAMPLE 7

7-(D-2-Aminophenylacetamido)-3-(4-methylthiazol-2-ylthiomethyl)-3-cephem-4-carboxylic acid When 2-mercapto-4-methylthiazole was reacted according to the procedure of Example 2 the title compound was obtained; m.p. 145°-149° (dec.).

Calculated for $C_{20}H_{20}N_4O_4S_3.H_2O$: C, 48.75; H, 4.48; N, 11.33; Found: C, 48.75; H, 4.36; N, 10.96.

EXAMPLE 8

7-(D-2-Aminophenylacetamido)-3-(5-methylthiazol-2-ylthiomethyl)-3-cephem-4-carboxylic acid When 2-mercapto-5-methylthiazole was used in the procedure of Example 2 the title compound was isolated as its zwitterion using the tributylamine method; m.p. 152°-157° (dec.);

Calculated for $C_{20}H_{20}N_4O_4S_3.H_2O$: C, 48.57; H, 4.48; N, 11.33; Found: C, 48.35; H, 4.29; N, 11.12.

EXAMPLE 9

7-(D-2-Aminophenylacetamido)-3-(thiazol-2-ylthiomethyl)-3-cephem-4-carboxylic acid When the procedure of Example 2 was followed with 2-mercaptothiazole the title compound was obtained using the tributylamine isolation method; m.p. 148°-152° (dec.);

Calculated for $C_{19}H_{18}N_4O_4S_3.H_2O$: C, 47.49; H, 4.19; N, 11.66; Found: C, 47.21; H, 4.02; N, 11.41.

EXAMPLE 10

7-(D-2-Aminophenylacetamido)-3-(isothiazol-5-ylthiomethyl)-3-cephem-4-carboxylic acid The title compound was obtained when 5-mercaptoisothiazole was reacted according to the procedure in Example 2 with the exception that $NaHCO_3$ was substituted for tri-n-butylamine; m.p. 171°-176° (dec.);

Calculated for $C_{19}H_{18}N_4O_4S_3.H_2O$: C. 47.48; H, 4.19; N, 11.66; Found: C, 47.20; H, 4.61; N, 11.59.

EXAMPLE 11

7-(D-2-Aminophenylacetamido)-3-(3-methylisothiazol-5-ylthiomethyl)-3-cephem-4-carboxylic acid To a solution of 3-methyl-5-bromoisothiazole (10.0 g., 0.056 mol.) [A. Adams and R. Slack, *J. Chem. Soc.*, 3061 (1959)] in dry tetrahydrofuran (100 ml.) at −70° was added over a 10 minute period an equal molar amount of n-butyl lithium in hexane. After stirring at −70° for 1 hour, sulfur (1.8 g., 0.056 mol.) was added. The mixture was stirred with continued cooling for 2.5 hours and then poured into ice water (200 ml.). The aqueous solution was extracted with ether and then lyophilized to give lithium 5-mercapto-3-methylisothiazole.

This product was then reacted according to the procedure of Example 2 to give the title compound; m.p. 157°–163° (dec.).

Calculated for $C_{20}H_{20}N_4O_4S_3$: C, 47.69; H, 4.60; N, 11.12; Found: C, 48.04; H, 4.28; N, 10.98.

EXAMPLE 12

7-(D-2-Aminophenylacetamido)-3-(2-thiazolin-2-ylthiomethyl)-3-cephem-4-carboxylic acid When 2-mercapto-2-thiazoline was reacted according to the procedure of Example 2 the title compound was obtained. The t-BOC protected product was purified by column chromatography on silica gel with 3% methanol in chloroform as eluent to give a residue which was dissolved in acetone and precipitated with petroleum ether. After the deblocking reaction, the zwitterionic product was isolated using the tributyl amine method; m.p. 158 (dec.);

Calculated for $C_{19}H_{20}N_4O_4S_3 \cdot \frac{3}{4} H_2O$: C, 47.69 H, 4.53; N, 11.71; Found: C, 47.95; H, 4.82; N, 11.36.

EXAMPLE 13

7-(D-2-Aminophenylacetamido)-3-(1,2,4-triazol-3-ylthiomethyl)-3-cephem-4-carboxylic acid When 3-mercapto-1,2,4-triazole was reacted according to the procedure of Example 2, the title compound was obtained; m.p. 185 (dec.).

Calculated for $C_{18}H_{18}N_6O_4S_2 \cdot H_2O$: C, 46.54; H, 4.34; N, 18.09; Found: C, 46.69; H, 4.35; N, 17.77.

EXAMPLE 14

7-(D-2-Aminophenylacetamido)-3-(2-methyl-1,2,4-triazole-3-ylthiomethyl)-3-cephem-4-carboxylic acid 3-Mercapto-2-methyl-1,2,4-triazole was reacted according to the procedure of Example 2 to yield the title compound; m.p. 220° (dec.);

Calculated for $C_{19}H_{20}N_6O_4S_2 \cdot \frac{1}{2} H_2O$: C, 48.60; H, 4.51; N, 17.90; Found: C, 48.82; H, 4.42; N, 17.78.

EXAMPLE 15

7-(D-2-Aminophenylacetamido)-3-(4-methyl-1,2,4-triazol-3-ylthiomethyl)-3-cephem-4-carboxylic acid When 3-mercapto-4-methyl-1,2,4-triazole was used in the procedure of Example 2, the title compound was obtained.

Calculated for $C_{19}H_{20}N_6O_4S_2 \cdot 2H_2O$: C, 45.96; H, 4.87; N, 16.92; Found: C, 45.51; H, 4.47; N, 16.60.

EXAMPLE 16

7-(D-2-Aminophenylacetamido)-3-(5-methyl-1,2,4-triazol-3-ylthiomethyl)-3-cephem-4-carboxylic acid The title compound was obtained when 3-mercapto-5-methyl-1,2,4-triazole was used in the procedure of Example 2.

Calculated for $C_{19}H_{20}N_6O_4S_2 \cdot 1.25 H_2O$: C, 47.24; H, 4.69; N, 17.29; Found: C, 47.39; H, 4.81; N, 16.80.

EXAMPLE 17

7-(D-2-Aminophenylacetamido)-3-(4-methyl-5-trifluoromethyl-1,2,4-triazol-3-ylthiomethyl)-3-cephem-4-carboxylic acid When 3-mercapto-4-methyl-5-trifluoromethyl-1,2,4-triazole was used in the procedure of Example 2, the title compound was obtained; m.p. 162°–165° (dec.);

Calculated for $C_{20}H_{19}F_3N_6O_4S_2 \cdot 1.5H_2O$: C, 43.24; H, 3.99; N, 15.13; Found: C, 43.63; H, 3.61; N, 14.70.

EXAMPLE 18

7-(D-2-Aminophenylacetamido)-3-(4-ethyl-1,2,4-triazol-3-ylthiomethyl)-3-cephem-4-carboxylic acid When 4-ethyl-3-mercapto-1,2,4-triazole was reacted according to the procedure of Example 2 the title compound was obtained.

Calculated for $C_{20}H_{22}N_6O_4S_2 \cdot 2H_2O$: C, 47.05; H, 5.13; N, 16.46; Found: C, 47.18; H, 4.57; N, 16.09.

EXAMPLE 19

7-(D-2-Aminophenylacetamido)-3-(1,3,4-oxadiazol-2-ylthiomethyl)-3-cephem-4-carboxylic acid The reaction of 2-mercapto-1,3,4-oxazole in the procedure of Example 2 gave the title compound as its zwitterion when t-butylamine was used in the tributylamine isolation method; m.p. 200° (dec.).

Calculated for $C_{18}H_{17}N_5O_5S_2 \cdot H_2O$: C, 46.44; H, 4.11; N, 15.04; Found: C, 46.12; H, 3.85; N, 14.54.

EXAMPLE 20

7-(D-2-Aminophenylacetamido)-3-(5-methyl-1,3,4-oxadiazol-2-ylthiomethyl)-3-cephem-4-carboxylic acid The title compound was obtained when 2-mercapto-5-methyl-1,3,4-oxadiazole was reacted according to the procedure of Example 2 with the exception that the t-BOC protected product was purified by chromatography on silica gel with 3:1 benzene:acetone as eluent; m.p. 240° (dec.).

Calculated for $C_{19}H_{19}N_5O_5S_2 \cdot 1.5 H_2O$: C, 46.71; H, 4.54; N, 14.33; Found: C, 46.67; H, 4.69; N, 13.80.

EXAMPLE 21

7-(D-2-Aminophenylacetamido)-3-(3-methyl-1,2,4-thiadiazol-5-ylthiomethyl)-3-cephem-4carboxylic acid When 5-mercapto-3-methyl-1,2,4-thiadiazole was reacted according to the procedure of Example 2, the title compound was obtained; m.p. 157° (dec.).

Calculated for $C_{19}H_{19}N_5O_4S_3 \cdot \frac{3}{4} H_2O$: C, 48.60; H, 4.63; N, 12.87; Found: C, 48.65, H, 4.87; N, 13.06.

EXAMPLE 22

7-(D-2-Aminophenylacetamido)-3-(1,3,4-thiadiazol-2-ylthiomethyl)-3-cephem-4-carboxylic acid When 2-mercapto-1,3,4-thiadiazole was used in the procedure of Example 2, the title compound was obtained; m.p. 170° (dec.).

Calculated for $C_{18}H_{17}N_5O_4S_3 \cdot H_2O$: C, 44.89; H, 3.55; N, 14.54; Found: C, 44.51; H, 3.87; N, 14.31.

EXAMPLE 23

7-(D-2-Aminophenylacetamido)-3-(5-ethyl-1,3,4-thiadiazol-2-ylthiomethyl)-3-cephem-4-carboxylic acid The title compound was obtained by reacting 5-ethyl-2-mercapto-1,3,4-thiadiazole in the procedure of Example 2 except that t-butylamine was substituted for tributylamine; m.p. 158°–160° (dec.).

Calculated for $C_{20}H_{21}N_5O_4S_3.H_2O$: C, 47.14; H, 4.55; N, 13.74; Found: C, 46.96; H, 4.33; N, 13.71.

EXAMPLE 24

7-(D-2-Aminophenylacetamido)-3-(1-methyltetrazol-5-ylthiomethyl)-3-cephem-4-carboxylic acid Reacting 5-mercapto-1-methyltetrazole according to the procedure of Example 2 gave the t-BOC protected compound which was purified by chromatography (silica gel and 4:1 benzene:acetone). When the deblocking reaction was ran for 10 minutes in cold trifluoroacetic acid, the title compound was obtained; m.p. 210°–211° (dec.).

Calculated for $C_{18}H_{19}N_7O_4S_2.\frac{1}{2} H_2O$: C, 45.96; H, 4.28; N, 20.84; Found: C, 46.30; H, 4.49; N, 20.08.

EXAMPLE 25

7-(D-2-Aminophenylacetamido)-3-(pyrazin-2-ylthiomethyl)-3-cephem-4-carboxylic acid When the procedure of Example 2 was used with 2-mercaptopyrazine, the title compound was obtained, m.p. 210° (dec.).

Calculated for $C_{20}H_{19}N_5O_4S_2.\frac{1}{2} H_2O$: C, 51.49; H, 4.32; N, 15.01; Found: C, 51.45; H, 4.24; N, 14.69.

EXAMPLE 26

7-(D-2-Aminophenylacetamido)-3-(4-methylpyrimid-2ylthiomethyl)-3-cephem-4-carboxylic acid The reaction of 2-mercapto-4-methylpyrimidine according to the procedure of Example 2 gave the title compound.

Calculated for $C_{21}H_{21}N_5O_4S_2.\frac{1}{2} H_2O$: C, 52.49; H, 4.61; N, 14.67; Found: C, 52.82; H, 4.56; N, 14.71.

EXAMPLE 27

7-(D-2-Aminophenylacetamido)-3-(pyrimid-2-ylthiomethyl)-3-cephem-4-carboxylic acid When 2-mercaptopyrimidine was reacted according to the procedure of Example 2, the title compound was obtained.

Calculated for $C_{20}H_{19}N_5O_4S_2.H_2O$: C, 50.51; H, 4.55; N, 14.73; Found: C, 50.71; H, 4.36; N, 14.53.

EXAMPLE 28

7-(D-2-Aminophenylacetamido)-3-(pyrimid-4-ylthiomethyl)-3-cephem-4-carboxylic acid When the procedure of Example 2 was used with 4-mercaptopyrimidine, the title compound was formed; m.p. 210° (dec.).

Calculated for $C_{20}H_{19}N_5O_4S_2.\frac{1}{2} H_2O$: C, 51.49; H, 4.32; N, 15.01; Found: C, 51.98; H, 4.15; N, 14.65.

EXAMPLE 29

7-(D-2-Aminophenylacetamido)-3-(5-n-butyl-1,3,4-thiadiazol-2-ylthiomethyl)-3-cephem-4-carboxylic acid The title compound was prepared when 5-n-butyl-2-mercapto-1,3,4-thiadiazole was reacted according to the procedure of Example 3 except that the acylation reaction was ran 0.5 hour at 0° and 2.5 hours at room temperature; m.p. 150°–151° (dec.).

Calculated for $C_{22}H_{25}N_5O_4S_3.H_2O$: C, 49.15; H, 5.06; N, 13.03; Found: C, 49.33; H, 4.83; N, 12.93.

EXAMPLE 30

7-(D-2-Aminophenylacetamido)-3-(2-methylpyrazin-3-ylthiomethyl)-3-cephem-4-carboxylic acid The title compound was prepared by the reaction of 3-mercapto-2-methylpyrazine according to the procedure of Example 2, m.p. 233° (dec.).

Calculated for $C_{21}H_{21}N_5O_4S_2.0.5 H_2O$: C, 52.49; H, 4.61; N, 14.67; Found: C, 52.89; H, 4.87; N, 14.77.

EXAMPLE 31

7-(D-2-Aminophenylacetamido)-3-(5-amino-1,3,4-thiadiazol-2-ylthiomethyl)-3-cephem-4-carboxylic acid When the procedure of Example 2 was used with 5-amino-2-mercapto-1,3,4-thiadiazole the title compound was obtained.

Calculated for $C_{18}H_{18}N_6O_4S_3.1.5 H_2O$: C, 42.76; H, 4.19; N, 16.62; Found: C, 42.84; H, 3.75; N, 16.66.

EXAMPLE 32

7-(D-2-Aminophenylacetamido)-3-(5-methylamino-1,3,4-thiadiazol-2-ylthiomethyl)-3-cephem-4-carboxylic acid When 2-mercapto-5-methylamino-1,3,4-thiadiazole was reacted according to the procedure of Example 2 the title compound was obtained; m.p. 210°.

EXAMPLE 33

7-(D-2-Aminophenylacetamido)-3-(5-acetamido-1,3,4-thiadiazol-2-ylthiomethyl)-3-cephem-4-carboxylic acid When the procedure of Example 2 was followed with 5-acetamido-2mercapto-1,3,4-thiadiazole the title compound was obtained; m.p. 188°–190° (dec.).

EXAMPLE 34

7-(D-2-Aminophenylacetamido)-3-(2-methylthiazol-5-ylthiomethyl)-3-cephem-4-carboxylic acid When 5-mercapto-2-methylthiazole was used in the procedure of Example 2 the title compound was prepared, m.p. 160°–194° (dec.).

EXAMPLE 35

When the appropriately substituted 3-mercapto-1,2,4-triazole was substituted for 3,4-dimethyl-5-mercapto-1,2,4-triazole in the procedure of Example 2 the following cephalosporins were obtained:

7-(D-2-aminophenylacetamido)-3-(1-ethyl-1,2,4-triazol-3-ylthiomethyl)-3-cephem-4-carboxylic acid 7-(D-2aminophenylacetamido)-3-(1-isopropyl-1,2,4-triazol-3-ylthiomethyl)-3-cephem-4-carboxylic acid 7-(D-2-aminophenylacetamido)-3-(4-n-propyl-1,2,4-triazol-3-ylthiomethyl)-3-cephem-4-carboxylic acid 7-(D-2-aminophenylacetamido)-3-(4-isopropyl-1,2,4-triazol-3-ylthiomethyl)-3-cephem-4-carboxylic acid 7-(D-2-aminophenylacetamido)-3-(4-n-butyl-1,2,4-triazol-3-ylthiomethyl)-3-cephem-4-carboxylic acid 7-(D-2-aminophenylacetamido)-3-(4-allyl-1,2,4-triazol-3-ylthiomethyl)-3-cephem-4-carboxylic acid 7-(D-2-aminophenylacetamido)-3-(5-ethyl-1,2,4-triazol-3-ylthiomethyl)-3-cephem-4-carboxylic acid 7-(D-2-aminophenylacetamido)-3-(5-n-propyl-1,2,4-triazol-3-ylthiomethyl)-3-cephem-4-carboxylic acid 7-(D-2-aminophenylacetamido)-3-(5-isopropyl-1,2,4-triazol-3-ylthiomethyl)-3-cephem-4-carboxylic acid 7-(D-2aminophenylacetamido)-3-(5-cyclopropyl-1,2,4-triazol-3-ylthiomethyl)-3-cephem-4-carboxylic acid 7-(D-2-aminophenylacetamido)-3-(5-methoxymethyl-1,2,4-triazol-3-ylthiomethyl)-3-cephem-4-carboxylic acid 7-(D-2-aminophenylacetamido)-3-(1-ethyl-5-methyl-1,2,4-triazol-3-ylthiomethyl)-3-cephem-4-carboxylic acid 7-(D-2-aminophenylacetamido)-3-(4-ethyl-5-methyl-1,2,4-triazol-3-ylthiomethyl)-3-cephem-4-carboxylic acid 7-(D-2-aminophenylacetamido)-3-(2,5-dimethyl-1,2,4-triazol-3-ylthiomethyl)-3-cephem-4-carboxylic acid.

EXAMPLE 36

7-(D-2-Aminophenylacetamido)-3-(1,2,3-triazol-5-ylthiomethyl)-3-cephem-4-carboxylic acid When 5-mercapto-1,2,3-triazole was reacted according to the procedure of Example 2 the title compound was prepared.

EXAMPLE 37

7-(D-2-Aminophenylacetamido)-3-(1-phenyltetrazol-5-ylthiomethyl)-3-cephem-4-carboxylic acid When 5-mercapto-1-phenyltetrazole was reacted according to the procedure of Example 2 the title compound was obtained.

EXAMPLE 38

7-(D-α-Amino-p-hydroxyphenylacetamido)-3-(5-methyl-1,3,4-thiadiazol-2-ylthiomethyl)-3-cephem-4-carboxylic acid An intimate mixture of D-p-hydroxyphenylglycine (3.34 g., 0.02 mol.) and MgO (1.61 g., 0.04 mol.) was suspended in 50% aqueous dioxane with stirring and T-butoxycarbonyl azide (5.72 g., 0.04 mol.) was added along with additional solvent (10 ml.). The reaction mixture was heated with stirring at 50° for 18 hours and then poured into cold water (250 ml.). The resultant solution was filtered, decolorized and extracted with ethyl acetate. The aqueous phase was covered with fresh ethyl acetate, cooled to 5°, and adjusted to pH 2.9 with 40% $H_3PO_4$. The aqueous layer was separated and re-extracted with ethyl acetate. The organic extracts were combined, dried and evaporated to give the N-t-butoxycarbonyl-p-hydroxyphenyl-glycine.

The above product (0.53 g., 2 mmol.) was dissolved in dry tetrahydrofuran (10 ml.) and triethylamine (0.28 ml., 2 mmol.) was added. The solution was cooled to −40° and a solution of trichloroacetyl chloride (0.36 g., 2 mmol.) in tetrahydrofuran (2.5 ml.) was added dropwise with stirring. After 20 minutes a cold (−43°) solution of 7-amino-3-(5-methyl-1,3,4-thiadiazol-2-ylthiomethyl)-3-cephem-4-carboxylic acid (0.69 g., 2 mmol.) and triethylamine (0.56 ml., 4 mmol.) in methylene chloride (30 ml.) was added. The reaction was stirred at −44° to −30° for 45 minutes and then allowed to warm to room temperature. The solution was filtered and the filtrate was evaporated to an oil which was dissolved in 2% $NaHCO_3$ solution and washed with ether. The aqueous solution was covered with ethyl acetate, cooled to 5°, and acidified to pH 3 with 40% $H_3PO_4$. Layers were separated and re-extracted with ethyl acetate. The combined extracts were dried and evaporated to give the t-butoxycarbonyl protected product.

The above product was treated for 4 minutes with cold glacial acetic acid which was saturated with HCl gas and then diluted with ether. The solid hydrochloride salt of the title compound was removed by filtration, washed with ether and dried. The zwitterionic product is obtained from the salt by standard methods.

EXAMPLE 39

Use of the t-butoxycarbonyl derivative of a p-chloro-α-aminophenylacetamido, p-nitro-α-aminophenylacetamido, 3,4-dimethoxy-α-aminophenylacetamido, 3-trifluoromethyl-α-aminophenylacetamido, α, p-diaminophenylacetamido (bis-derivative), or p-methyl-α-aminophenylacetamidocephalosporanic acid in the procedure of Example 1 gives the corresponding 7-(α-amino substituted phenylacetamido)-3-(5-methyl-1,3,4-thiadiazol-2-ylthiomethyl)-3-cephem-4-carboxylic acid.

EXAMPLE 40

When an equivalent amount of the appropriate heterocyclic thiol is substituted for 5-methyl-2-mercapto-1,3,4-thiadiazole in the procedure of Example 1, the following cephalosporins are obtained:

3-(1-methylimidazol-2-ylthiomethyl)-7-(D-α-aminophenylacetamido)-3-cephem-4-carboxylic acid 3-(1,5-dimethylimidazol-2-ylthiomethyl)-7-(Dα-aminophenylacetamido)-3-cephem-4-carboxylic acid 3-(oxazol-2-ylthiomethyl)-7-(D-aminophenylacetamido)-3-cephem-4-carboxylic acid 3-(5-methyloxazol-2-ylthiomethyl)-7-(D-α-aminophenylacetamido)-3-cephem-4-carboxylic acid 3-(imidazol-2-ylthiomethyl)-7-(D-α-aminophenylacetamido)-3-cephem-4-carboxylic acid 3-(4(5)-methylimidazol-2-ylthiomethyl)-7-(D-α-aminophenylacetamido)-3-cephem-4-carboxylic acid 3-(4,5-dimethylimidazol-2-ylthiomethyl)-7-(D-α-aminophenylacetamido)-3-cephem-4-carboxylic acid 3-(4,5-dimethylthiazol-2-ylthiomethyl)-7-(D-α-aminophenylacetamido)-3-cephem-4-carboxylic acid 3-(5-aminothiazol-2-ylthiomethyl)-7-(D-α-aminophenylacetamido)-3-cephem-4-carboxylic acid 3-(2-imidazolin-2-ylthiomethyl)-7-(D-α-aminophenylacetamido)-3-cephem-4-carboxylic acid 3-(1-ethyl-1H-tetrazol-5-ylthiomethyl)-7-(D-α-aminophenylacetamido)-3-cephem-4-carboxylic acid.

EXAMPLE 41

When an equivalent amount of 3-amino-5-mercapto-1,2,4-triazole, 1-phenyl-5-mercapto-3-methyl-1H-1,2,4-triazole, 3-phenyl-5-mercapto-1,2,4-triazole, 5-amino-3-mercapto-1,2,4-thiadiazole, 1-benzyl-1H-tetrazole-5-thiol or 1-propyl-1H-tetrazole-5-thiol is substituted for 5-methyl-2-mercapto-1,3,4-thiadiazole in the procedure of Example 1, the corresponding 3-heterocyclicthiomethyl-7-(D-α-aminophenylacetamido)-3-cephem-4-carboxylic acid is obtained.

EXAMPLE 42

When an equivalent amount of one of the heterocyclic thiols listed below is substituted for 2-mercapto-5-methyl-1,3,4-thiadiazole in the procedure of Example 1, the corresponding 3-(heterocyclicthiomethyl)-7-(D-α-aminophenylacetamido)-3-cephem-4-carboxylic acid is obtained:

2-mercapto-5-phenyl-1,3,4-oxadiazole
2-mercapto-5-propyl-1,3,4-oxadiazole
5-benzyl-2-mercapto-1,3,4-oxadiazole
2-mercapto-5-phenyl-1,3,4-thiadiazole
5-benzyl-2-mercapto-1,3,4-thiadiazole
3-mercapto-5-methyl-1,2,4-thiadiazole
3-mercapto-1,2,4-thiadiazole
5-mercapto-1,2,4-thiadiazole
5-mercapto-3-phenyl-1,2,4-thiadiazole
2-amino-4-mercaptopyrimidine
2-amino-4-mercapto-6-methylpyrimidine
2-mercapto-s-triazine
2-mercapto-4-methyl-s-triazine
3-mercapto-as-triazine
5,6-dimethyl-3-mercapto-as-triazine
1,5-dimethyl-3-mercaptopyrazole
3-mercaptopyridazine
6-bromo-3-mercaptopyridazine
3-mercapto-6-methylpyridazine
2-mercaptopyridine
4-mercaptopyridine
2-mercapto-6-methylpyridine
2-mercapto-5-nitropyridine
2-mercaptopurine
6-mercaptopurine
8-mercaptopurine
2-amino-6-mercaptopurine
4-mercapto-1H-pyrazolo[3,4-d]pyrimidine
2-mercapto-5-pyridinecarboxamide
5-amino-2-mercaptopyridine

EXAMPLE 43

When an equivalent amount of the t-butoxycarbonyl derivative of 7-(3,4-dichloro-α-aminophenylacetamido)-cephalosporanic acid, 7-(4-hydroxymethyl-α-aminophenylacetamido)cephalosporanic acid, 7-(4-aminomethyl-α-aminophenylacetamido)-cephalosporanic acid, 7-(3,5-dihydroxy-α-aminophenylacetamido)cephalosporanic acid, 7-(3-chloro-4-hydroxy-α-aminophenylacetamido)cephalosporanic acid, 7-(2-chloro-4-hydroxy-α-aminophenylacetamido)cephalosporanic acid, 7-(2-fluoro-4-hydroxy-α-aminophenylacetamido)cephalosporanic acid, 7-(3-fluoro-4-hydroxy-α-aminophenylacetamido)cephalosporanic acid, 7-(4-isopropyl-α-aminophenylacetamido)cephalosporanic acid, 7-(4-bromo-α-aminophenylacetamido)cephalosporanic acid, 7-(3-fluoro-α-aminophenylacetamido)-cephalosporanic acid, or 7-(2-chloro-α-aminophenylacetamido)cephalosporanic acid is substituted for the starting material in the procedure of Example 1, the corresponding 7-substituted α-aminophenylacetamido-3-(5-methyl-1,3,4-thiadiazol-2ylthiomethyl)-3-cephem-4-carboxylic acid is obtained.

EXAMPLE 44

To a 250 ml. round-bottom flask equipped with a CaSO₄ drying tube and magnetic stirring and containing 0.01 mole of N-t-butoxycarbonyl-L-methionine in 25 ml. of dry tetrahydrofuran is added an equimolar amount of N,N'-carbonyldiimidazole in one portion as a solid. Stirring is continued for about 30 minutes and then a solution of an equimolar amount of the product of Example 1 in tetrahydrofuran is added in one portion. The mixture is then stirred until reaction is complete. The solvent is removed under vacuum and the residue dissolved in a solvent such as ethyl acetate or ether. The resulting solid imidazole salt of the protected methionylcephalosporin is filtered off, dissolved in a mixture of methanol and acetone, and stirred with excess Amberlite IR 120H ion exchange resin (previously washed with methanol) to remove the imidazole. The resin is filtered off and the filtrate evaporated to give 7-(α-t-butoxycarbonyl-L-methionyl-aminophenylacetamido)-3-(5-methyl-1,3,4-thiadiazol-2-ylthiomethyl)-3-cephem-4-carboxylic acid.

To an ice-cold 100 ml. round bottom flask equipped with a CaSO₄ drying tube and magnetic stirring and containing 30 ml. of trifluoroacetic acid is added 0.005 mole of the above compound in one portion as a solid. After stirring for about 1 hour, the ice bath is removed and the reaction mixture allowed to warm to room temperature. About one-half of the trifluoroacetic acid is removed under vacuum and the remaining solution poured into 400 ml. of dry ether with rapid stirring. The resulting solid is collected by filtration to give the trifluoroacetate salt of the desired product, 7-(α-L-methionyl-aminophenylacetamido)-3-(5-methyl-1,3,4-thiadiazol-2-ylthiomethyl)-3-cephem-4-carboxylic acid. This solid is dissolved in a mixture of water and acetone and most of the acetone is stripped off under vacuum. The solid is filtered off and the filtrate in a stirred ice-cooled flask brought to pH of about 4.0–4.5 by slowly adding 5% NaHCO₃. The mixture is refrigerated and the product obtained as a white precipitate.

The product may also be isolated from its trifluoroacetate salt by stirring its aqueous solution with 25% Amberlite LA-1 (acetate form) ion exchange resin in methyl isobutyl ketone or Amberlite IR-45 resin (acetone-washed).

EXAMPLE 45

When the product of Example 1 is treated with acetic acid, propionic acid, butyric acid, or octanoic acid activated by prior reaction with N,N'-carbonyldiimidazole, all according to the procedure in the first part of Example 44, the corresponding 7-(α-alkanoylaminophenylacetamido)-3-(5-methyl-1,3,4-thiadiazol-2-ylthiomethyl)-3-cephem-4-carboxylic acid is obtained.

EXAMPLE 46

When an equivalent amount of N-t-butoxycarbonylglycine, N-t-butoxycarbonylalanine, or N,N'-bis(t-butoxycarbonyl)lysine is substituted for N-t-butoxycarbonylmethionine in the procedure of Example 44, the corresponding 7-(α-acylaminophenylacetamido)-3-(5-methyl-1,3,4-thiadiazol-2-ylthiomethyl)-3-cephem-4-carboxylic acid is obtained.

EXAMPLE 47

When an equivalent amount of N-t-butoxycarbonylphenylalanine is substituted in the procedure of Example 44, 7-(α-phenylalanylaminophenylacetamido)-3-(5-methyl-1,3,4-thiadiazol-2-ylthiomethyl)-3-cephem-4-carboxylic acid is obtained.

EXAMPLE 48

When an equivalent amount of N-t-butoxycarbonyl-L-aspartic acid β-t-butyl ester is substituted in the procedure of Example 44, 7-(α-L-aspartoylaminophenylacetamido)-3-(5-methyl-1,3,4-thiadiazol-2-ylthiomethyl)-3-cephem-4-carboxylic acid is obtained.

The glutamoyl analog is prepared in the same manner.

EXAMPLE 49

When an equivalent amount of azidoacetic acid is substituted in the first part of Example 44, 7-(α-azidoacetamidophenylacetamido)-3-(5-methyl-1,3,4-thiadiazol-2-ylthiomethyl)-3-cephem-4-carboxylic acid is obtained.

Reduction of the azido group by hydrogenation using a prereduced suspension of 5% Pd/BaSO$_4$ in methanol acidified with 5% conc. HCl gives the glycine analog, which is also prepared by using N-t-butoxycarbonylglycine in the procedure of Example 44.

EXAMPLE 50

When an equivalent amount of N-t-butoxycarbonyl-2,2-dimethylthiazolidine-4-carboxylic acid is used in the procedure of Example 44, 7-(α-cysteinylaminophenylacetamido)-3-(5-methyl-1,3,4-thiadiazol-2-ylthiomethyl)-3-cephem-4-carboxylic acid is obtained.

EXAMPLE 51

When an equivalent amount of N-t-butoxycarbonyl-O-(2,2,2-trifluoro-1-benzyloxycarbonylaminoethyl)-L-serine is used in the procedure of Example 44, 7-(α-serylaminophenylacetamido)-3-(5-methyl-1,3,4-thiadiazol-2-ylthiomethyl)-3-cephem-4-carboxylic acid is obtained.

The threonylmandelamido analog is prepared in the same manner.

EXAMPLE 52

When an equivalent amount of methoxyacetic acid is substituted in the first part of Example 44, 7-(α-methoxyacetamidophenylacetamido)-3-(5-methyl-1,3,4-thiadiazol-2-ylthiomethyl)-3-cephem-4-carboxylic acid is obtained.

Ethoxyacetyl, propoxypropionyl, and methoxybutyryl analogs are prepared in analogous fashion.

EXAMPLE 53

When 2-mercapto-1,3,4-thiadiazole is used in the procedure of Example 1 and the resulting product treated with chloroacetic acid according to the first part of Example 44, 7-(α-chloroacetamidophenylacetamido)-3-(1,3,4-thiadiazol-2-ylthiomethyl)-3-cephem-4-carboxylic acid is obtained.

Preparation of chloropropionyl, bromoacetyl, and chlorobutyryl analogs is accomplished in the same manner.

EXAMPLE 54

When 2-mercaptothiazole is used in the procedure of Example 1 and the resulting product treated with methylthioacetic acid according to the first part of Example 44 7-(α-methylthioacetamidophenylacetamido)-3-(thiazol-2-ylthiomethyl)-3-cephem-4-carboxylic acid is obtained.

The ethylthioacetyl and methylthiobutyryl analogs are prepared in the same manner.

EXAMPLE 55

When 2-mercaptoimidazole is used in the procedure of Example 1 and the resulting product treated with phenoxyacetic acid according to the first part of Example 44, 7-(α-phenoxyacetamidophenylacetamido)-3-(imidazol-2-ylthiomethyl)-3-cephem-4-carboxylic acid is obtained.

EXAMPLE 56

When 2-mercapto-5-ethyloxazole is used in Example 1 and the resulting product treated with β-allyloxypropionic acid according to the first part of Example 44, 7-(α-allyloxypropionamidophenylacetamido)-3-(5-ethyloxazol-2-ylthiomethyl)-3-cephem-4-carboxylic acid is obtained.

EXAMPLE 57

When an equivalent amount of O-(2,2,2-trichloroethoxycarbonyl)glycolic acid is reacted with the product of Example 1, according to the first part of Example 44, and the resulting intermediate stirred with zinc dust in glacial acetic acid, 7-(α-glycoloylaminophenylacetamido)-3-(5-methyl-1,3,4-thiadiazol-2-ylthiomethyl)-3-cephem-4-carboxylic acid is obtained.

EXAMPLE 58

Use of an equivalent amount of cyanoacetic acid in the first part of Example 44 gives 7-(α-cyanoacetamidophenylacetamido)-3-(5-methyl-1,3,4-thiadiazol-2-ylthiomethyl)-3-cephem-4-carboxylic acid.

EXAMPLE 59

Use of an equivalent amount of t-butoxycarbonylpropionic acid in the procedure of Example 44 gives 7-(α-carboxypropionamidophenylacetamido)-3-(5-methyl-1,3,4-thiadiazol-2-ylthiomethyl)-3-cephem-4-carboxylic acid.

Use of a carbalkoxypropionic acid gives a corresponding carbalkoxypropionyl product.

EXAMPLE 60

Use of an equivalent amount of isonicotinic acid, p-nitrobenzoic acid, benzoic acid, o-toluic acid, m-anisic acid, m-chlorobenzoic acid, m-trifluoromethylbenzoic acid, 5-methyl-2-furoic acid, picolinic acid, nicotinic acid, thiophene-2-carboxylic acid, 4-methyloxazole-5-carboxylic acid, 1,2,3-triazole-4-carboxylic acid, p-fluorobenzoic acid, or p-cyanobenzoic acid in the first part of Example 44 gives the corresponding α-carbocyclic or heterocyclic acylaminophenylacetamido-3-(5-methyl-1,3,4-thiadiazol-2-ylthiomethyl)-3-cephem-4-carboxylic acid.

The p-nitro compound is catalytically reduced with a 5% Pd on C catalyst to the p-amino compound.

EXAMPLE 61

Use of the t-butoxycarbonyl derivative of a p-chloro-α-aminophenylacetamido, p-hydroxy-α-aminophenylacetamido, p-nitro-α-aminophenylacetamido, p-hydroxy-m-methoxy-α-aminophenylacetamido, 3,4-dimethoxy-α-aminophenylacetamido, p-methoxy-m-hydroxy-α-aminophenylacetamido, 3-trifluoromethyl-α-aminophenylacetamido, 3,4-dihydroxy-α-aminophenylacetamido, α, p-diaminophenylacetamido (bis-derivative), p-hydroxymethyl-α-aminophenylacetamido, p-aminomethyl-α-aminophenylacetamido, 3,5-dihydroxy-α-aminophenylacetamido, 2-chloro-4-hydroxy-α-aminophenylacetamido, 3-chloro-4-hydroxy-α-aminophenylacetamido, 2-fluoro-4-hydroxy-α-aminophenylacetamido, 3-fluoro-4-hydroxy-α-aminophenylacetamido, or p-methyl-α-aminophenylacetamidocephalosporanic acid and 5-methyl-3-mercapto-1,2,4-triazole in the procedure of Example 1 gives the corresponding 7-(α-amino substituted phenylacetamido)-3-(5-methyl-1,2,4-triazol-3-ylthiomethyl)-3-cephem-4-carboxylic acid.

EXAMPLE 62

Use of 1-methyl-5-mercapto-1,2,3-triazole, 1-ethyl-5-mercapto-1,2,3-triazole, 4-methyl-5-mercapto-1,2,3-triazole, 4,5-diethyl-3-mercapto-1,2,4-triazole, 4-ethyl-3-mercapto-5-methyl-1,2,4-triazole, 5-ethyl-3-mercapto-4-methyl-1,2,4-triazole, 2-mercaptoimidazole, or 2-mercaptooxazole in the procedure of Example 2 gives the corresponding 7-(α-aminophenylacetamido)-3-(heterocyclic thiomethyl)-3-cephem-4-carboxylic acid.

EXAMPLE 63

Use of an equivalent amount of isonicotinic acid, p-nitrobenzoic acid, benzoic acid, o-toluic acid, m-anisic acid, m-chlorobenzoic acid, m-trifluoromethylbenzoic acid, 5-methyl-2-furoic acid, picolinic acid, nicotinic acid, thiophene-2-carboxylic acid, 4-methyloxazole-5-carboxylic acid, 1,2,3-triazole-4-carboxylic acid, p-fluorobenzoic acid, or p-cyanobenzoic acid and the product from Example 16 in the procedure of Example 44 gives the corresponding 0-carbocyclic or heterocyclic acylmandelamido-3-(5-methyl-1,2,4-triazol-3-ylthiomethyl)-3-cephem-4-carboxylic acid.

The p-nitro compound is catalytically reduced with a 5% Pd on C catalyst to the p-amino compound.

EXAMPLE 64

Use of 7-(D-α-aminophenylacetamido)-3-(5-methyl-1,2,4-triazol-3-ylthiomethyl)-3-cephem-4-carboxylic acid in the procedure of Example 44 gives 7-(D-α-methionylaminophenylacetamido)-3-(5-methyl-1,2,4-triazol-3-ylthiomethyl)-3-cephem-4-carboxylic acid.

EXAMPLE 65

Use of other acylating agents as specified in Examples 45–59 according to the procedure of Examples 44 and 64, using the same starting cephalosporin as in Example 64, gives the corresponding 7-acylated aminophenylacetamidocephalosporin product.

EXAMPLE 66

7-(D-2-Aminophenylacetamido)-3-(1H-tetrazol-5-ylthiomethyl)-3-cephem-4-carboxylic acid To a solution of 7-ACA (13.7 g., 0.05 mol.) and NaHCO$_3$ (12.69 g., 0.15 mol.) in acetone (125 ml.) was added 5-mercapto-1H-tetrazole (7.71 g., 0.075 mol.). The mixture was heated to reflux over a 1.5 hour period during which time additional NaHCO$_3$ (4.23 g., 0.05 mol.) was added to maintain the solution at pH 7. The cooled solution was acidified to pH 2 and the solid was collected, washed with acetone and ether, and dried.

To a cold solution of D-α-t-butoxycarboxamidophenylacetic acid (4.01 g., 0.016 mol.) and 2,4-dinitrophenol (2.93 g., 0.016 mol.) in dry tetrahydrofuran (50 ml.) was added N,N-dicyclohexylcarbodiimide (3.28 g., 0.016 mol.). The reaction was allowed to come to room temperature and was stirred two hours. The urea was removed by filtration and the filtrate was evaporated in vacuo to give the activated ester.

The above 7-ACA compound (5.0 g., 0.016 mol.) and triethylamine (3.22 g., 0.032 mol.) were stirred and cooled in dry tetrahydrofuran (50 ml.). The activated ester was added and the solution was stirred several hours at 0° and then overnight at room temperature. The solution was diluted with water, adjusted to pH 1, and extracted with ethyl acetate. The extracts were washed with water, dried and concentrated in vacuo to a residue which was dissolved in ethanol and precipitated with ether.

This product was treated with cold trifluoroacetic acid (60 ml.). The excess acid was evaporated in vacuo and the residue was triturated with ether to give the title compound as its trifluoroacetic acid salt; m.p. 200° (dec.).

Calculated for $C_{17}H_{17}N_7O_4S_2 \cdot C_2HF_3O_2$: C, 40.64; H, 3.23; N, 17.46; Found: C, 40.79; H, 3.64; N, 17.64.

EXAMPLE 67

Use of 3-mercapto-1-n-propyl-1,2,4-triazole, 3-mercapto-2-n-propyl-1,2,4-triazole, 3-mercapto-4,5-di-n-propyl-1,2,4-triazole, 3-mercapto-2-isopropyl-1,2,4-triazole, 3-mercapto-4,5-diisopropyl-1,2,4-triazole, 1-allyl-3-mercapto-1,2,4-triazole, 2-allyl-3-mercapto-1,2,4-triazole, 5-allyl-3-mercapto-1,2,4-triazole, 4,5-diallyl-3-mercapto-1,2,4-triazole, 1-cyclopropyl-3-mercapto-1,2,4-triazole, 2-cyclopropyl-3-mercapto-1,2,4-triazole, 4-cyclopropyl-3-mercapto-1,2,4-triazole, and 4,5-dicyclopropyl-3-mercapto-1,2,4-triazole in the procedure of Example 2 gives the corresponding 7-(D-2-aminophenylacetamido)-3-(substituted-1,2,4-triazol-3-thiomethyl)-3-cephem-4-carboxylic acid.

EXAMPLE 68

2-Mercapto-5-trifluoromethyl-1,3,4-thiadiazole

To a rapidly stirred suspension of copper bronze (6.1 g.) in 48% HBr (975 ml.) was added over a 1 hour period and cooling to −15° a mixture of NaNO$_2$ (195 g., 2.83 mol.) and 2-amino-5-trifluoromethyl-1,3,4-thiadiazole (103 g., 0.61 mol.) [I. Lalezari and N. Sharghi, *J. Hetero. Chem.* 3:336 (1966)]. The resultant mixture was stirred for 0.75 hour with ice bath cooling and for 1.5 hour without cooling. The mixture was adjusted to pH 8 using 50% NaOH and maintaining the temperature below 20°. Saturated sodium bisulfite was added until a negative starch-iodide test was obtained. The mixture was made strongly acidic with HCL and extracted with petroleum ether. The extracts were washed with water, dried (MgSO$_4$) and evaporated to the product. Distillation gave 2-bromo-5-trifluoromethyl-1,3,4-thiadiazole; b.p 56°–57°/11 mm.

A mixture of the above product (77.7 g., 0.334 mol.), thiourea (27 g., 0.355 mol.), and ethanol (235 ml.) was refluxed for 1 hour. After cooling the reaction, a solution of KOH (43.4 g.) in water 135 ml.) was added and the solution was refluxed for 20 minutes. The ethanol was removed in vacuo and the aqueous residue was extracted with ether which was discarded. The product was precipitated by acidification of the aqueous phase and was collected. An ethereal solution of the product was dried, treated with decolorizing carbon, and evaporated in vacuo to give the title compound; m.p. 72°–73°. Calculated for $C_3HF_3N_2S_2$: C, 19.35; H, 0.54; N, 15.05; S, 34.44; Found: C, 19.26; H, 0.56; N, 14.82; S, 34.25.

EXAMPLE 69

When D-p-hydroxyphenylglycine is reacted with the appropriate 7-amino-3-heterocyclicthiomethyl-3-cephem-4-carboxylic acid according to the procedure of Example 38 the following compounds are obtained:

7-(D-α-amino-p-hydroxyphenylacetamido)-3-1-methyltetrazol-5-ylthiomethyl)-3-cephem-4-carboxylic acid 7-(D-α-amino-p-hydroxyphenylacetamido)-3-(5-methyl-1,3,4-oxadiazol-2-ylthiomethyl)-3-cephem-4-carboxylic acid 7-(D-α-amino-p-hydroxyphenylacetamido)-3-(4-methyl-1,2,4-triazol-3-ylthiomethyl)-3-cephem-4-carboxylic acid 7-(D-α-amino-p-hydroxyphenylacetamido)-3-(4,5-dimethyl-1,2,4-triazol-3-ylthiomethyl)-3-cephem-4-carboxylic acid 7-(D-α-amino-p-hydroxyphenylacetamido)-3-(1,2,3-triazol-5-ylthiomethyl)-3-cephem-4-carboxylic acid 7-(D-α-amino-p-hydroxyphenylacetamido)-3-(1-methyl-1,2,3-triazol-5-ylthiomethyl)-3-cephem-4-carboxylic acid.

EXAMPLE 70

When D-3,4-dihydroxyphenylglycine is substituted for D-p-hydroxyphenylglycine in Examples 38 and 69 the corresponding 7-(D-α-amino-3,4-dihydroxyphenylacetamido)-3-(heterocyclicthiothiomethyl)-3-cephem-4-carboxylic acid is obtained.

EXAMPLE 71

When D-4-hydroxy-3-methoxyphenylglycine is substituted for D-p-hydroxyphenylglycine in Examples 38 and 69, the corresponding 7-(D-α-amino-4-hydroxy-3-methoxyphenylacetamido)-3-heterocyclicthiomethyl-3-cephem-4-carboxylic acid is formed.

EXAMPLE 72

When D-3-hydroxy-4-methoxyphenylglycine is substituted for D-p-hydroxyphenylglycine in Examples 38 and 69, the corresponding 7-(D-α-amino-3-hydroxy-4-methoxyphenylacetamido)-3-heterocyclicthiomethyl-3-cephem-4-carboxylic acid is obtained.

EXAMPLE 73

An injectable pharmaceutical composition is prepared by dissolving 500 mg. of sodium 7-(α-aminophenylacetamido)-3-(5-methyl-1,2,4-triazol-3-ylthiomethyl)-3-cephem-4-carboxylate in 2 ml. of sterile water on normal saline solution.

Any of the above disclosed cephalosporins may be formulated in a similar manner.

EXAMPLE 74

An antibacterial capsule has the following components: cephalosporin (500 mg.), lactose (250 mg.) and magnesium stearate (75 mg.).

Due to the presence of both an amine group and a carboxylic acid group in the cephalosporin compounds of this invention, it is possible, by standard methods, to prepare both acid and base salts of pharmaceutically acceptable nontoxic acids and bases. It is to be understood that these salts are included within the scope of this invention.

We claim:

1. A pharmaceutical composition comprising an antibacterially-effective amount of a compound of the formula

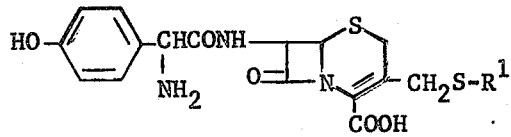

in which:
R¹ is tetrazol-5-yl, 1,3,4-thiadiazol-2-yl, 1,3,4-oxadiazol-2-yl, 1,2,4-triazol-3-yl, or 1,2,3-triazol-5-yl, each of such groups being unsubstituted or substituted with one or two lower alkyl groups of one to four carbon atoms,
or a nontoxic, pharmaceutically acceptable salt thereof;
and a pharmaceutically acceptable carrier therefor.

2. A pharmaceutical composition according to claim 1, in which R¹ is 1,2,4-triazol-3-yl or 1,2,3-triazol-5yl, unsubstituted or substituted with one or two lower alkyl groups of one to four carbon atoms.

3. A pharmaceutical composition according to claim 1, in which the compound is 7-(α-amino-p-hydroxyphenylacetamido)-3-(5-methyl-1,3,4-thiadiazol-2-ylthiomethyl)-3-cephem-4-carboxylic acid or a nontoxic, pharmaceutically acceptable salt thereof.

4. A pharmaceutical composition according to claim 1, in which the compound is 7-(α-amino-p-hydroxyphenylacetamido)-3-(1-methyltetrazol-5-ylthiomethyl)-3-cephem-4-carboxylic acid or a nontoxic pharmaceutically acceptable salt thereof.

5. A pharmaceutical composition according to claim 2, in which the compound is 7-(α-amino-p-hydroxyphenylacetamido)-3-(5-methyl-1,2,4-triazol-3-ylthiomethyl)-3-cephem-4-carboxylic acid or a nontoxic pharmaceutically acceptable salt thereof.

6. A pharmaceutical composition according to claim 2, in which the compound is 7-(α-amino-p-hydroxyphenylacetamido)-3-(4,5-dimethyl-1,2,4-triazol-3-ylthiomethyl)-3-cephem-4-carboxylic acid or a nontoxic pharmaceutically acceptable salt thereof.

7. A pharmaceutical composition according to claim 1, in which the compound is 7-(α-amino-p-hydroxyphenylacetamido)-3-(5-methyl-1,3,4-oxadiazol-2-ylthiomethyl)-3-cephem-4-carboxylic acid or a nontoxic pharmaceutically acceptable salt thereof.

8. A pharmaceutical composition according to claim 2, in which the compound is 7-(α-amino-p-hydroxyphenylacetamido)-3-(1,2,3-triazol-5-ylthiomethyl)-3-cephem-4-carboxylic acid or a nontoxic pharmaceutically acceptable salt thereof.

9. A pharmaceutical composition according to claim 8, in which the compound is 7-(D-α-amino-p-hydroxyphenylacetamido)-3-(1,2,3-triazol-5-ylthiomethyl)-3-cephem-4-carboxylic acid or a nontoxic pharmaceutically acceptable salt thereof.

10. A pharmaceutical composition according to claim 2, in which the compound is 7-(α-amino-p-hydroxyphenylacetamido)-3-(1-methyl-1,2,3-triazol-5-ylthiomethyl)-3-cephem-4-carboxylic acid or a nontoxic pharmaceutically acceptable salt thereof.

* * * * *